United States Patent
Wright et al.

(10) Patent No.: US 10,755,909 B2
(45) Date of Patent: Aug. 25, 2020

(54) CHEMICAL ANALYSIS DEVICE AND METHOD

(71) Applicant: INFICON, Inc., East Syracuse, NY (US)

(72) Inventors: Kenneth C. Wright, Fayetteville, NY (US); Jaime L. Winfield, Canastota, NY (US); Peter Santariello, Marcellus, NY (US)

(73) Assignee: INFICON, Inc., East Syracuse, NY (US)

( * ) Notice: Subject to any disclaimer, the term of this patent is extended or adjusted under 35 U.S.C. 154(b) by 0 days.

(21) Appl. No.: 16/406,573

(22) Filed: May 8, 2019

(65) Prior Publication Data

US 2019/0348267 A1   Nov. 14, 2019

Related U.S. Application Data

(60) Provisional application No. 62/668,493, filed on May 8, 2018.

(51) Int. Cl.
| | | |
|---|---|---|
| H01J 49/04 | (2006.01) | |
| G16C 20/70 | (2019.01) | |
| H01J 49/00 | (2006.01) | |

(52) U.S. Cl.
CPC .......... *H01J 49/0427* (2013.01); *G16C 20/70* (2019.02); *H01J 49/0031* (2013.01); *H01J 49/0468* (2013.01)

(58) Field of Classification Search
CPC ............... H01J 49/0427; H01J 49/0031; H01J 49/0468; G16C 20/70
See application file for complete search history.

(56) References Cited

U.S. PATENT DOCUMENTS

| 5,448,062 A | 9/1995 | Cooks et al. |
| 6,923,939 B1 | 8/2005 | Nayar et al. |

(Continued)

FOREIGN PATENT DOCUMENTS

| CN | 205112500 U | 3/2016 |
| EP | 1974895 A2 | 10/2008 |

(Continued)

OTHER PUBLICATIONS

PCT/US2019/031328; filed May 8, 2019; International Search Report and Written Opinion; dated Jul. 12, 2019; 13 pages.

*Primary Examiner* — Nicole M Ippolito
*Assistant Examiner* — Hanway Chang
(74) *Attorney, Agent, or Firm* — Barclay Damon LLP

(57) ABSTRACT

Methods and systems for chemical analysis. For instance, a device for chemical analysis of a sample includes a housing, an inlet, a pump, multiple membranes and at least one detector. The housing contains an interior chamber of the device. The inlet on the housing introduces the sample into the interior chamber. The pump is connected to the housing to form a partial vacuum in the interior chamber. The multiple membranes have different response times to different constituents of the sample. The multiple membranes include at least a first membrane and a second membrane. At least one of the first membrane and the second membrane comprises a tubular portion. The multiple membranes have different response times to different constituents of the sample. The detector is for detecting the different constituents of the sample after interaction with the multiple membranes. In addition, a method for chemical analysis of a sample. A first step includes introducing a sample to multiple membranes having different response times to different constituents of the sample. A second step includes separating the different constituents of the sample due to the different response times of the multiple membranes. A third step (Continued)

includes detecting the different constituents of the gas after separating with the multiple membranes.

20 Claims, 15 Drawing Sheets

(56) References Cited

U.S. PATENT DOCUMENTS

2012/0208004 A1  8/2012  Wolcott et al.
2016/0225597 A1  8/2016  Wright et al.

FOREIGN PATENT DOCUMENTS

EP  2368704 A2  9/2011
WO  2008/038070 A1  4/2008
WO  2018/203275 A1  11/2018

CHEMICAL ANALYSIS DEVICE AND METHOD

CROSS-REFERENCE TO RELATED APPLICATION(S)

This application claims priority to U.S. Provisional Patent Application Ser. No. 62/668,493, filed May 8, 2018, which is incorporated herein by reference in its entirety.

TECHNICAL FIELD

The present application generally relates to analytical systems such as chemical analyzers, and in particular to rapid response mass analysis techniques.

BACKGROUND

One of the limitations of conventional chemical analysis devices is that they are not readily deployable in the field, in order to allow rapid assessment of potential dangerous chemicals that may be present in a monitoring area, such as an airport, building, etc., because they require fixed installations. Another limitation of conventional techniques is that analysis cannot be conducted rapidly because the techniques occur in a monolithic process that takes quite some time to complete. A further limitation of conventional techniques relates to the fact that certain different molecules have the same profile when analyzed under mass spectroscopy, for instance, and are not readily differentiated from one another, leading to potential false positives when screening or monitoring for a specific target molecule.

SUMMARY

Methods and devices for chemical analysis are presented. In one aspect, a device for chemical analysis of a sample includes a housing, an inlet, a pump, multiple membranes and at least one detector. The housing contains an interior chamber of the device. The inlet on the housing introduces the sample into the interior chamber. The pump is connected to the housing to form a partial vacuum in the interior chamber. The multiple membranes have different response times to different constituents of the sample. The multiple membranes include at least a first membrane and a second membrane. At least one of the first membrane and the second membrane comprises a tubular portion. The multiple membranes have different response times to different constituents of the sample. The detector is for detecting the different constituents of the sample after interaction with the multiple membranes.

In another aspect, a method for chemical analysis of a sample is presented. A first step includes introducing a sample to multiple membranes having different response times to different constituents of the sample. A second step includes separating the different constituents of the sample due to the different response times of the multiple membranes. A third step includes detecting the different constituents of the gas after separating with the multiple membranes.

In a further aspect, a device for chemical analysis of a sample includes a housing, an inlet, a pump, multiple membranes, at least one detector, and at least one heating element. The chamber is for receiving the sample. The multiple membranes have different response times to different constituents of the sample. The multiple membranes at least partially disposed in the chamber. The detector is disposed in the chamber and for detecting the different constituents of the sample after interaction with the multiple membranes. The detector includes a mass spectrometer. The at least one heating element is disposed near at least one of the multiple membranes. The at least one heating element is configured to heat the at least one of the multiple membranes to facilitate different response times of the different constituents.

The above embodiments are exemplary only. Other embodiments are within the scope of the disclosed subject matter.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the disclosed subject matter encompasses other embodiments as well. The drawings are not necessarily to scale, emphasis generally being placed upon illustrating the features of certain embodiments of the invention. In the drawings, like numerals are used to indicate like parts throughout the various views.

DETAILED DESCRIPTION

Figure 1:
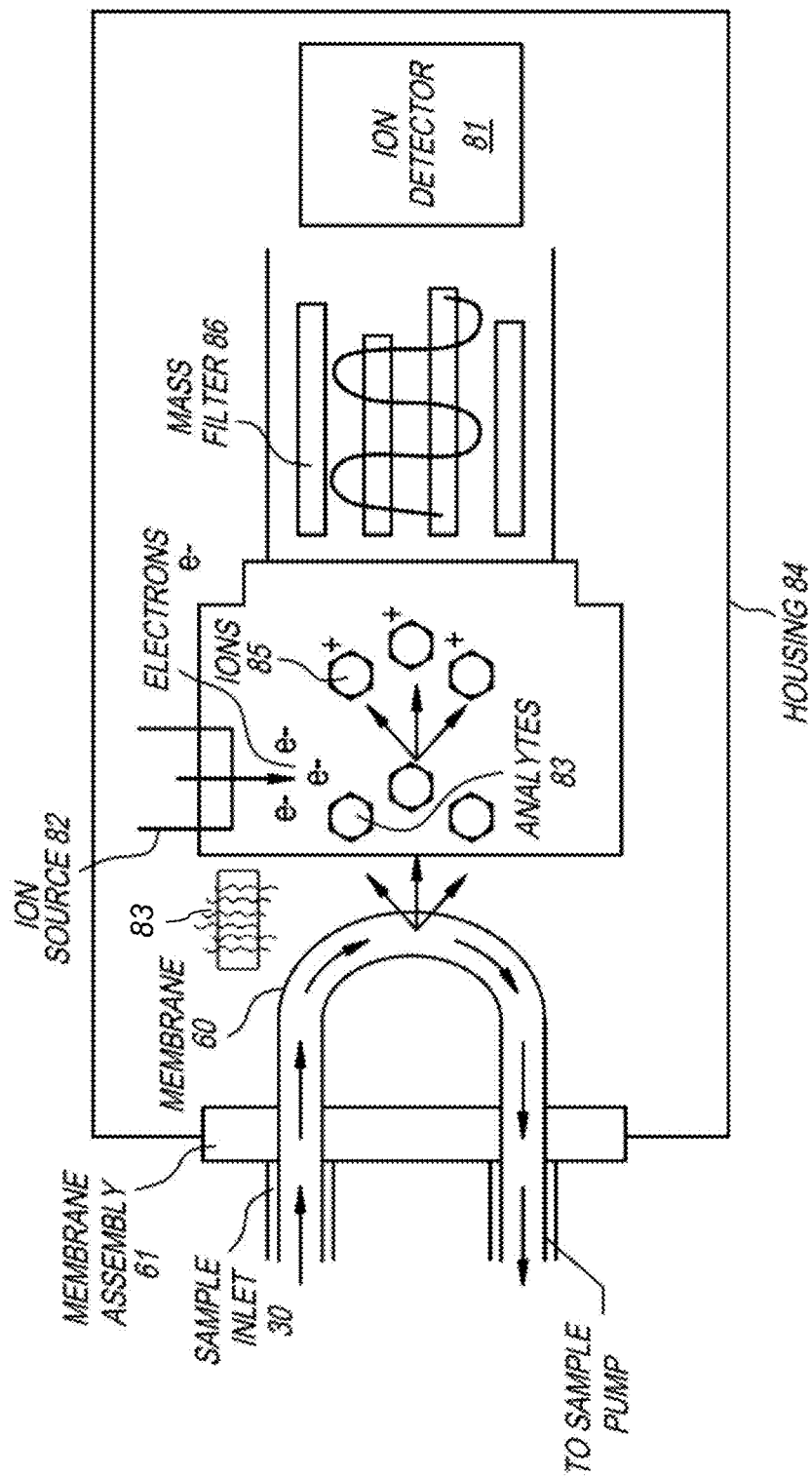
FIGS. 1-2 are schematic views of exemplary systems, in accordance with aspects set forth herein.

Embodiments of the disclosed subject matter provide techniques for chemical analysis. Other embodiments are within the scope of the disclosed subject matter.

The present invention provides, in part, techniques and systems for rapid detection of potentially hazardous gases or volatile organic compounds, such as chemical weapons, present in the parts per billion or parts per trillion concentration in the air. Of course, the present techniques are not limited to detection of chemical weapons, and may be used in industrial and other applications involving toxic chemicals. For instance, VX nerve gas, sarin, phosgene, mustard gas, chlorine, cyanide compounds, etc., are all candidate chemicals that may be detected rapidly using the techniques herein described.

Applicants have discovered that certain membranes have different interaction times with different molecules, and if a chemical analyzer is configured to include one or more such membranes, the different molecules can pass through the membranes with some degree of time separation. Although the time separation will not generally be perfect, enough separation may be introduced by the membranes, so that mass spectroscopy or other detector techniques may be used to identify the components of the gas down to parts per billion or trillion in a rapid manner. In some examples described below, the physical separation with the membranes may be paired with analytical techniques.

Generally stated, provided herein, in one aspect, is a device for chemical analysis of a sample includes a housing, an inlet, a pump, multiple membranes and at least one detector. The housing contains an interior chamber of the device. The inlet on the housing introduces the sample into the interior chamber. The pump is connected to the housing to form a partial vacuum in the interior chamber. The multiple membranes have different response times to different constituents of the sample. The multiple membranes include at least a first membrane and a second membrane. At least one of the first membrane and the second membrane comprises a tubular portion. The multiple membranes have different response times to different constituents of the sample. The detector is for detecting the different constituents of the sample after interaction with the multiple membranes. In one embodiment, the detector includes a mass spectrometer. In another embodiment, the device further includes a chamber for introducing the sample to the multiple membranes.

In an exemplary implementation, the multiple membranes are exposed to the sample sequentially. In another implementation, the multiple membranes are exposed to the sample in parallel. In yet a further embodiment, the multiple membranes have different response times to multiple constituents having a specific mass to charge ratio.

In one embodiment, the device further including a heating element to facilitate the different response times of the different constituents. In another embodiment, the different constituents include different molecules. In a further embodiment, the detector is configured to perform a first detection of the sample after interacting with a first of the multiple membranes to determine a preliminary result, and if the preliminary result indicates a likelihood of an outcome, perform a second detection of the sample after interacting with a second of the multiple membranes to determine a final result.

In a specific embodiment, the device comprises a handheld structure such as a wand, and the wand includes the chamber, membranes, detector, heating element, battery, microcontroller, etc. In such a case, the an inlet on the wand allows for a first analysis of the sample (e.g., collected by waving or holding the wand in the air), this first analysis being done rapidly. Continuing with this example, the first analysis may rule out the presence of certain molecules, such as toxic molecules, in which case the analysis is completed. However, the first analysis may indicate a potential presence of a certain molecule, and a second analysis would then be queued up by the inlet (or another inlet) allowing the air to interact with a second membrane that takes a longer amount of time before analysis. Such a two-stage (or, generalizing, n-stage) analysis can facilitate an operator of the handheld chemical analysis device to rapidly screen an area or targets.

In another aspect, a method for chemical analysis of a sample is presented. A first step includes introducing a sample to multiple membranes having different response times to different constituents of the sample. A second step includes separating the different constituents of the sample due to the different response times of the multiple membranes. A third step includes detecting the different constituents of the gas after separating with the multiple membranes.

In one embodiment of the method, separating the different constituents of the sample includes starting and stopping a flow of the sample. In another embodiment, introducing the sample includes introducing the sample to a first of the multiple membranes at a first time and a second of the multiple membranes at a second time after the first time. In a further embodiment, the method also includes detecting a preliminary result after introducing the sample to the first of the multiple membranes at the first time, and if the preliminary result indicates a likelihood of an outcome, detecting a final result after introducing the sample to the second of the multiple membranes at the second time. By way of example, the sample may be introduced to the multiple membranes at a same time or sequentially.

In a further aspect, a device for chemical analysis of a sample includes a housing, an inlet, a pump, multiple membranes, at least one detector, and at least one heating element. The chamber is for receiving the sample. The multiple membranes have different response times to different constituents of the sample. The multiple membranes at least partially disposed in the chamber. The detector is disposed in the chamber and for detecting the different constituents of the sample after interaction with the multiple membranes. The detector includes a mass spectrometer. The at least one heating element is disposed near at least one of the multiple membranes. The at least one heating element is configured to heat the at least one of the multiple membranes to facilitate different response times of the different constituents. In different examples, the multiple membranes are exposed to the sample sequentially or in parallel. As implemented, the multiple membranes may have different response times to multiple constituents having a specific mass to charge ratio.

FIG. 1 schematically shows a system in which a membrane assembly 60 is positioned at the inlet of a chemical analyzer housing 84 that includes an ion source 82 positioned at the inlet side of the housing. The interior of housing 84 can be pumped down to vacuum, e.g., by a pump. The ion source includes a filament (not shown) or other means for producing a stream of electrons (e−) that are injected into an ionization volume or chamber along with a sample gas 83, which includes analytes, which passes through the membrane assembly 60 at the inlet 30 of the chemical analyzer housing 84. Impact by the electrons with the incoming molecules of the sample gas 83 produces the formation of positive ions 85 that are caused to be accelerated into a mass spectrometer mass filter 86, such as a quadrupole mass filter, in which masses are scanned for detection by a sensor such as an ion detector 81, having an electron multiplier or a Faraday cup, which is disposed at the opposite end of the housing 84 from the inlet 30.

In various aspects, different valves may be disposed within or near the membrane assembly 61 to allow the sample gas 83, having an analyte, or a mixture or composition containing the analyte, to be applied to membrane assembly 60. The gas supply can include a pump adapted to either apply positive pressure to push material towards membrane 60 or to apply negative pressure to pull material across membrane 60.

In an example, the analytes of interest of the gas 83 are non-polar molecules that are more soluble in the membrane 60 material than the bulk gas (e.g. air) or liquid (e.g. water).

Therefore, gas 83 has a much higher concentration of the analyte than the original sample.

In an example, Dow Corning™ Silastic™ Q7-4750 biomedical/pharmaceutical grade platinum-cured silicone material may be used as a membrane.

By way of example, different membranes that have different permeations rates for different molecules may be used either individually or in combination. By using multiple membranes, better separation may be achieved using one material compared to another. In addition, the rate through a first membrane material could be compared to the rate through a second membrane material, in a multiple membrane embodiment of the system described herein. In such a case, the relative rate differences of passage through the two different membranes could help define the molecule, and separate the molecule from background noise from other chemicals.

It should be noted that one goal is for separation is to stop the flow of new sample to the membrane. After stopping the flow, the gas that is present will go through the one or more membranes at its own rate, which may be dependent on the membrane composition, thickness and physical geometry. By contrast, if the sample flow is not stopped, new sample arriving to the membrane would just keep flowing through the membrane and separation in time would not be achieved.

Many schemes use a PDMS membrane material; non-polar molecules pass through the PDMS membrane material quickly and polar molecules do not.

Continuing with FIG. 1, the membrane 60 is a tube that passes through the chamber, which is, e.g., pumped down to low pressures. A sample pump draws a stream of carrier fluid through the tube; the carrier fluid transports the analyte. This system advantageously permits trapping many contaminants at the entrance to the tube so analytes can flow through portions of the tube downstream of the entrance. Some analytes pass through the membrane 60 into the vacuum chamber and are detected by the detector 81. Exemplary detectors include, but are not limited, to, mass spectrometers (e.g., time of flight, quadrupole mass sensor, ion trap, or magnetic sector); photoionization detectors; optical detectors (e.g., to detect fluorescence, absorbance, or Raman scattering); metal oxide sensors; and quartz crystal micro balances. Some sensing technologies employ a vacuum in the housing of the chamber and some do not. The atmospheric composition and pressure inside the housing 84 can be selected based on the analytes to be detected and the operation of the detector. In various aspects, the MIMS system is used as a detection unit in a continuous process monitor (CPM). Instead of an inlet, the system is attached to a chamber or device in the process to be monitored. The membrane is directly exposed to the fluid (e.g., gas) in the chamber or device.

A heater 83 may be deployed to heat the membrane 60. For example, the heater 83 can be irradiate the membrane 60 with photons (e.g., infrared) from an LED or diode laser. This permits heating only the membrane by picking a wavelength preferentially absorbed by the membrane, and doing so in a non-contact manner. Fast heating and cooling (no thermal mass in direct contact with membrane) can be performed. The diodes or other radiation sources can be arranged in the vacuum system or chamber. Any number of sources can be used, e.g., one more-powerful source or an array of less-powerful sources. Notably, as an advantage, the use of multiple membranes directly reduces the number of false positive detection events while simultaneously reducing the total detection time required to sweep a given area.

Figure 2:
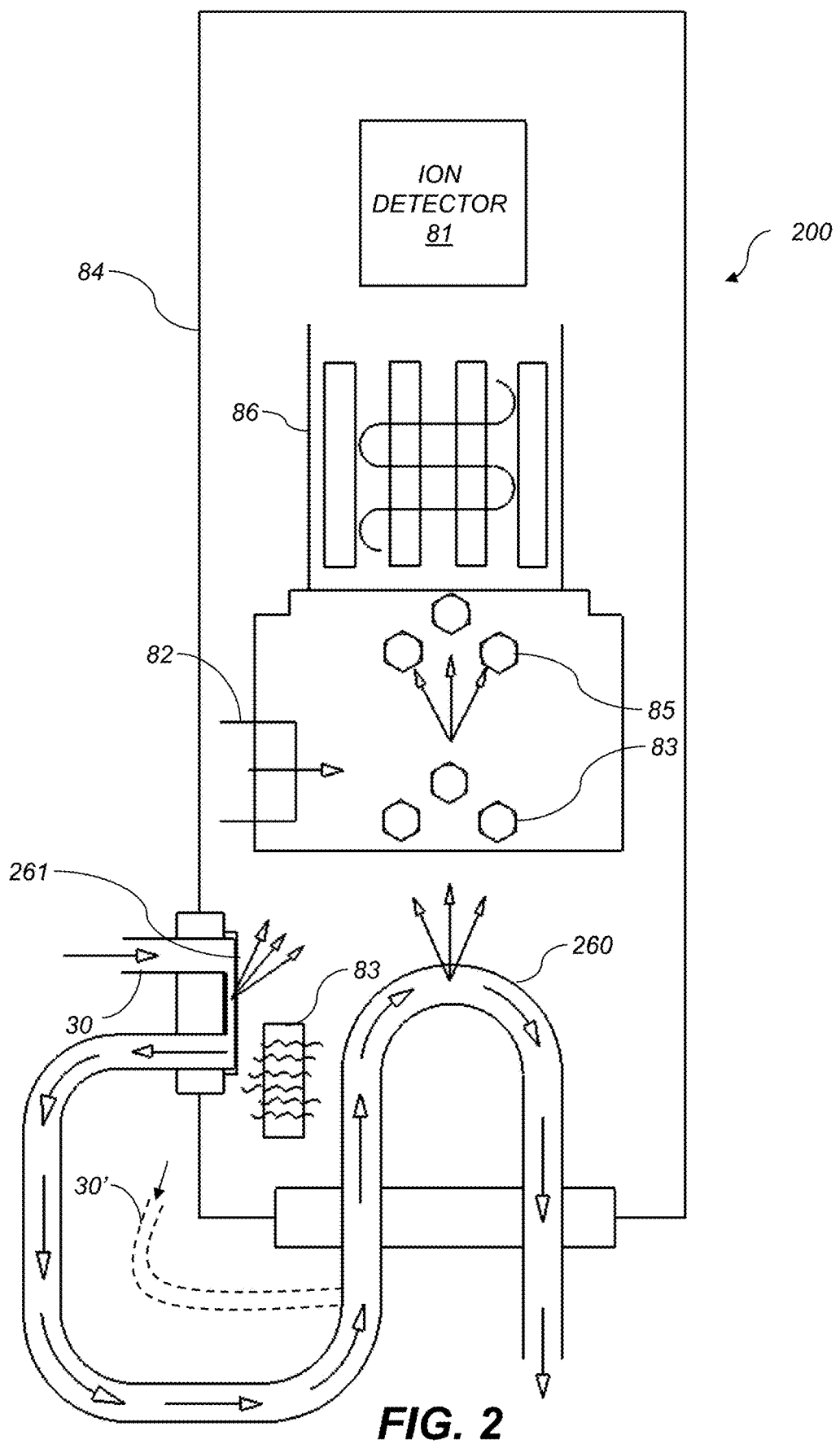

Turning next to FIG. 2, a two-membrane system 200 is described. As depicted, a first thin membrane 261 and a second membrane 260 are deployed in system 200. In one example, a valve (not shown) may be deployed along the flow path from membrane 261 to membrane 260, so that only one membrane is exposed to the sample at a time. In other examples, both membranes may be in fluid communication with the sample at the same time. In the example of FIG. 2, an optional second inlet 30' is depicted in dashed lines, which, if provisioned, would allow the sample to be introduced to both membranes 260 and 261 in parallel. This alternate embodiment would facilitate parallel introduction of the sample to both membranes, rather than a serial arrangement in which the inlet first introduces the sample to membrane 260 and then next introduces the sample to a membrane 261.

Other examples could include three, four, five, or more different membranes, which are connected via a system of pumps and/or valves. The membranes may have different chemical compositions and thicknesses, and may be designed to help separate different chemicals. The membranes may be sequential or in parallel with the sample inlet. The membranes may be flat thin membranes like membrane 261, or may be tubular shaped membranes like membrane 260. By way of operational overview, the system described in either FIG. 1 or FIG. 2 may be deployed within a portable test set, having a wand for intake of atmospheric air. In such a case, the wand can include the intake port for delivering the atmospheric sample to the membrane. A person of ordinary skill in the art would readily understand that one or more valves and/or pumps may be deployed in the system to allow the gas to impinge upon one or more of the membranes.

FIGS. 3A-3E are flowchart of exemplary methods for analyzing chemicals, in accordance with aspects set forth herein. Beginning with FIG. 3A, a method 300A uses a single membrane system such as that described in FIG. 1. After the method 300A starts, at block 304 a mixture is continuously applied to the membrane. The mixture may include, for example, multiple chemical components for separation. Next, at block 306, the detector, such as the mass spectrometer, measures the analytes in the chamber. Assuming, for example, nothing beyond normal atmospheric compounds are present, the system may determine that no further analysis is required, and at block 308 does not initiate separation, at block 318 determines the analytes in the sample gas, and at block 320 continues measuring by returning to block 304.

Figure 3A:
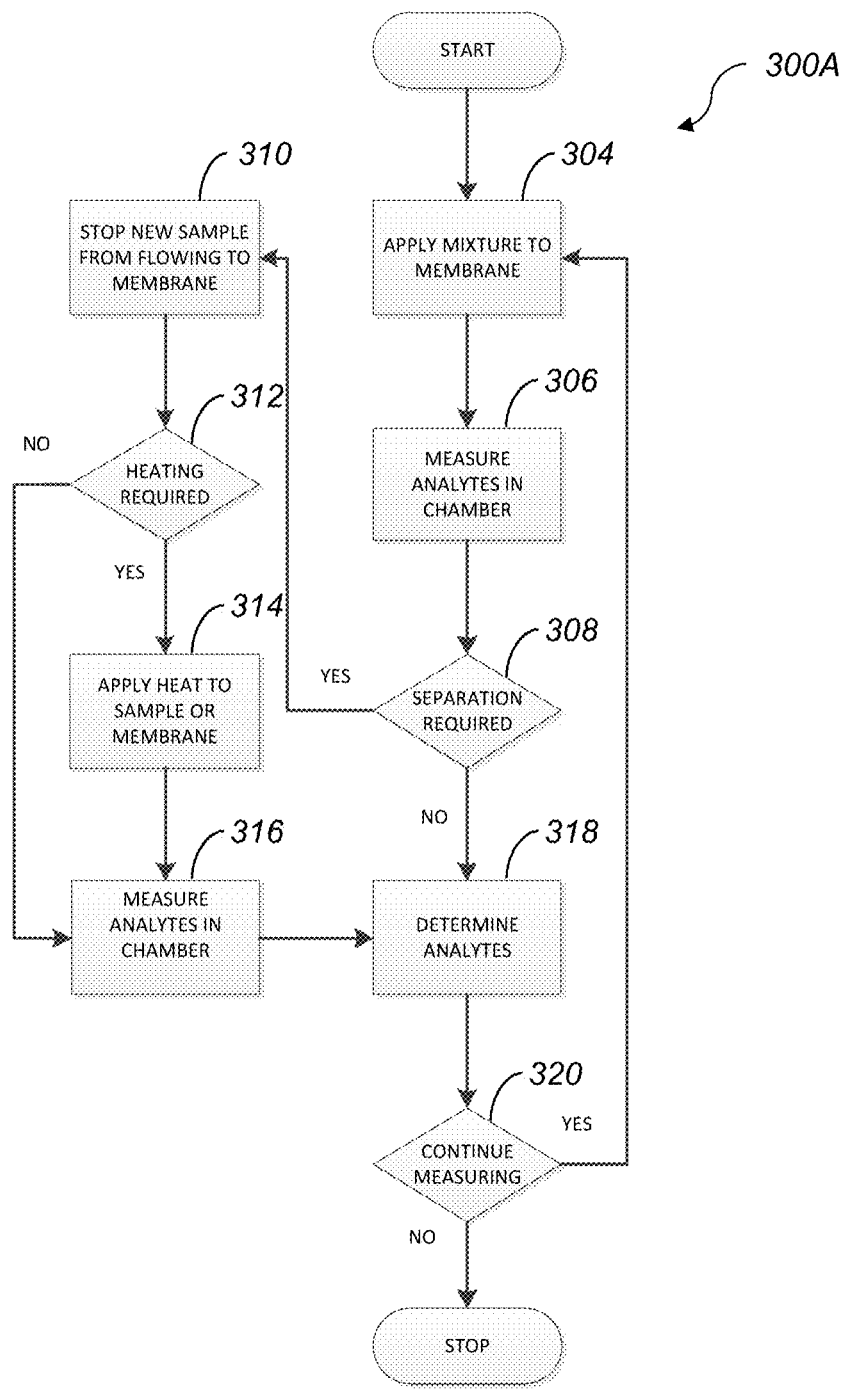
FIGS. 3A-3E are flowcharts of exemplary methods for analyzing chemicals, in accordance with aspects set forth herein.

In another example of FIG. 3A, at block 308, based on the preliminary measurement while the sample gas is continuously applied to the membrane, the method 300A may determine that separation is required. For instance, enough signal may be detected to show the presence of some volatile organic compounds. Upon separation being required at block 308, at block 310, the sample flow to the membrane is stopped, e.g., using a valve. By stopping the sample flow at block 310, whatever sample is already in the system and membrane can pass through the membrane to the detector over a period of one or more seconds.

In a further example, at block 312, the method 300A may decide that heating the sample is desirable. For instance, the preliminary measurement at block 306 may indicate the possible presence of some analytes of interest that can be further time separated by heating of the membrane. Next, at block 314, heat is applied to the sample and/or the membrane. Note that in other embodiments, blocks 312 and 314 could also be reversed, with the heat being applied before the sample flow is stopped, depending on how fast the membrane could be heated to assist in the separation of the analytes in the sample.

Continuing with the method 300A of FIG. 3A, at block 316 the detector may measure the analytes in the chamber. As explained in further detail below, this measurement step now has the benefit of the time separation caused by the membrane (either heated or unheated as the case may be). Thus, at block 318, the determination of analytes can be possible and/or more accurate than without separation.

Figure 3B:
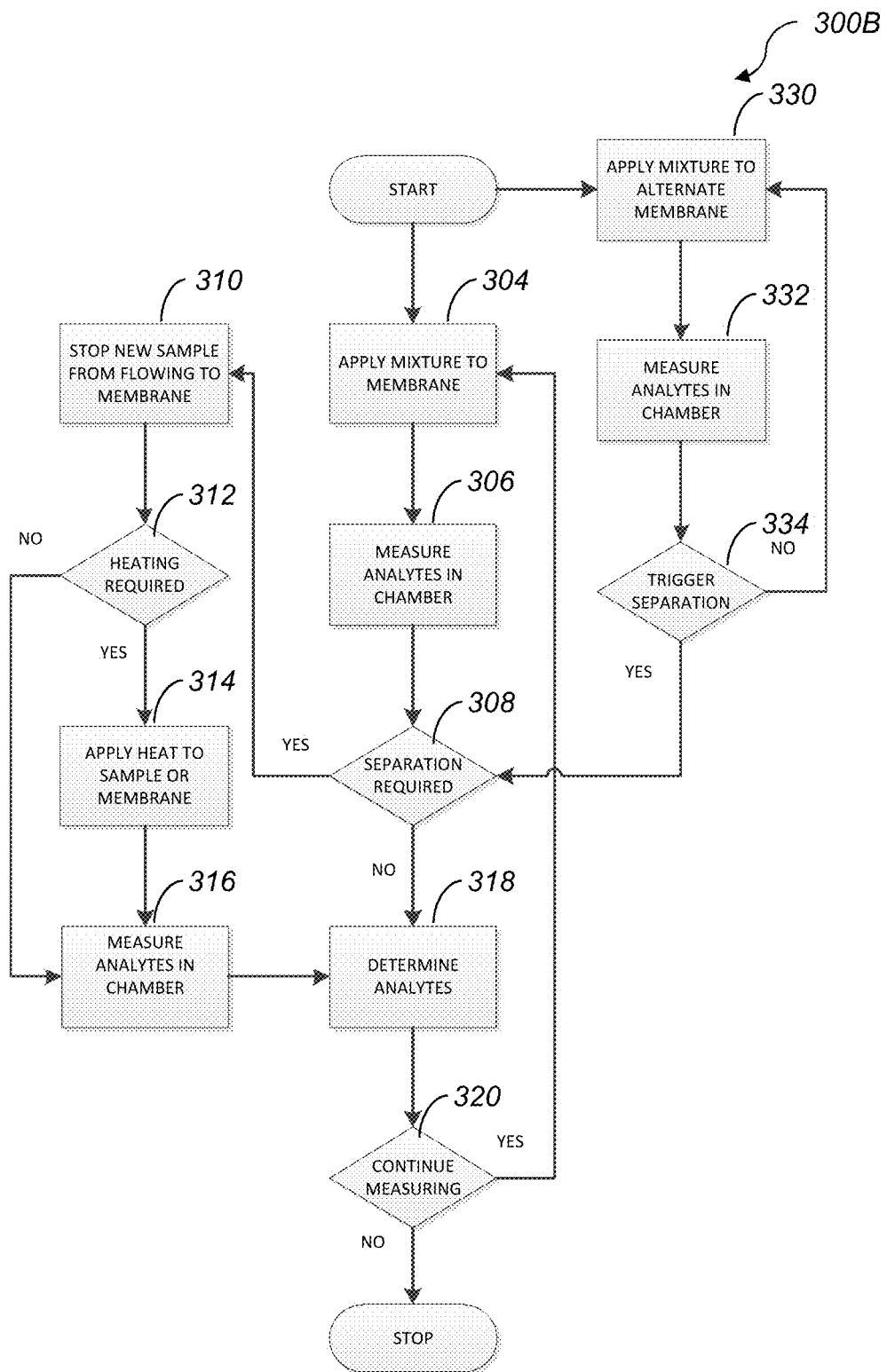

FIG. 3B depicts a method 300B, which uses the system 200 of FIG. 2, having a first (e.g., alternate) membrane 261 (FIG. 2) as well as the membrane 260 (FIG. 2). In such a case, at block 330 of the method 300B, the sample mixture is applied to the alternate membrane 261. For instance, membrane 261 may be a thinner membrane of the same composition (or even a different composition) as the membrane 260, and thus may allow for less overall time separation of the mixture, but at a much higher speed. Then, at block 332 the analytes are measured in the chamber, and although the membrane 261 may not provide enough resolution to determine with 99% confidence the chemical composition of the gas, enough information would be present to trigger the use of the membrane 260. In such a case, at block 334, the method would proceed to block 308, and the method would continue through blocks 310-320 as described previously with respect to FIG. 3A. Notably, during a rapid response detection mode, the system could continuously loop through blocks 330-334, using the thinner membrane 261, looking for an indication that further action is required. For instance, the system may be deployed in a wand which emits a low volume beeping sound indicating that nothing is amiss. In such a case, as soon as (at block 332) a possibility of specified chemicals is detected, the wand could emit a louder beep indicating to the user that the wand should be held at that spot and that the method is triggering separation and analysis.

Figure 3C:
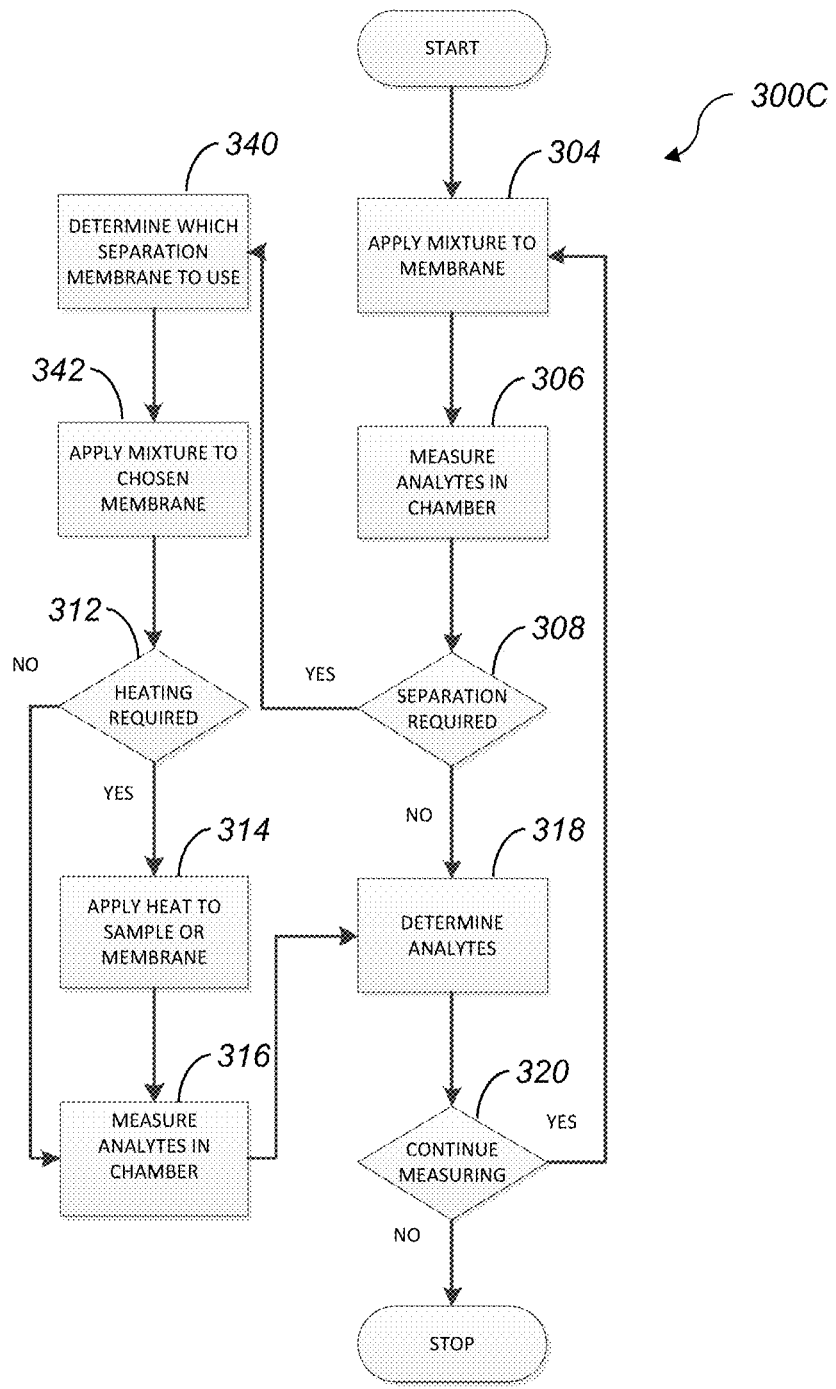

Turning next to FIG. 3C, yet another embodiment of a method 300C starts and proceeds through blocks 304-308 as described above with respect to method 300A (FIG. 3A) or method 300B (FIG. 3B), but differs in the determination of required separation at block 308. In the depicted embodiment, the method 300C at block 340 then determines which of several different separation membranes to use at block 340. Then, using valves and/or pumps, the method 300C at block 342 applies the gas sample mixture to the selected or chosen membrane. For example, based on the initial, preliminary analysis performed at block 306, the system may have narrowed down the possible chemical components to a smaller subset, and can then map the possible subset to a particular membrane that is more amenable to separation of those chemical components, and may or may not enable heating. Subsequently, the method 300C proceeds through blocks 312-320 as described above with respect to methods 300A (FIG. A) or method 300B (FIG. B).

Figure 3D:
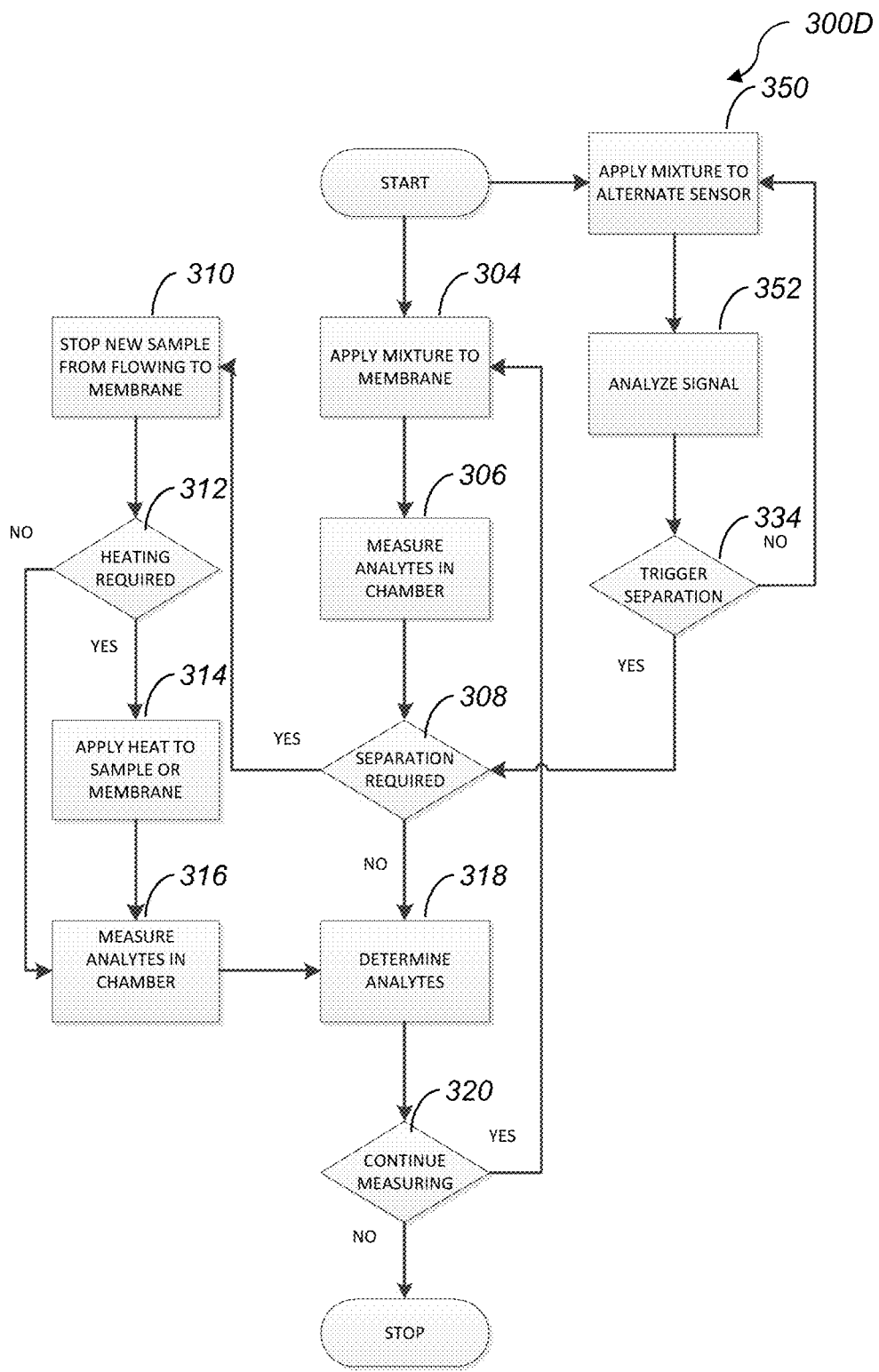

In another example, FIG. 3D discloses a method 300D that starts and then applies the sample gas mixture to an alternate sensor at block 350. For example, the alternate sensor may be a different mass spectrometer, or may be an ion mobility spectrometer, or any other analytical sensor for determining chemical species present in a gas or fluid. By way of explanation, as noted before, the multiple stage system disclosed herein allows for an initial, or preliminary test to trigger a subsequent, more accurate detector. Advantageously, the combination of different detectors allows for a more rapid overall detection. Next, the method 300D at block 352 analyzes the signal from the alternate sensor, and proceeds to block 334 to trigger separation, and proceeds through blocks 304-320, as described above with respect to method 300B (FIG. 3B).

Figure 3E:
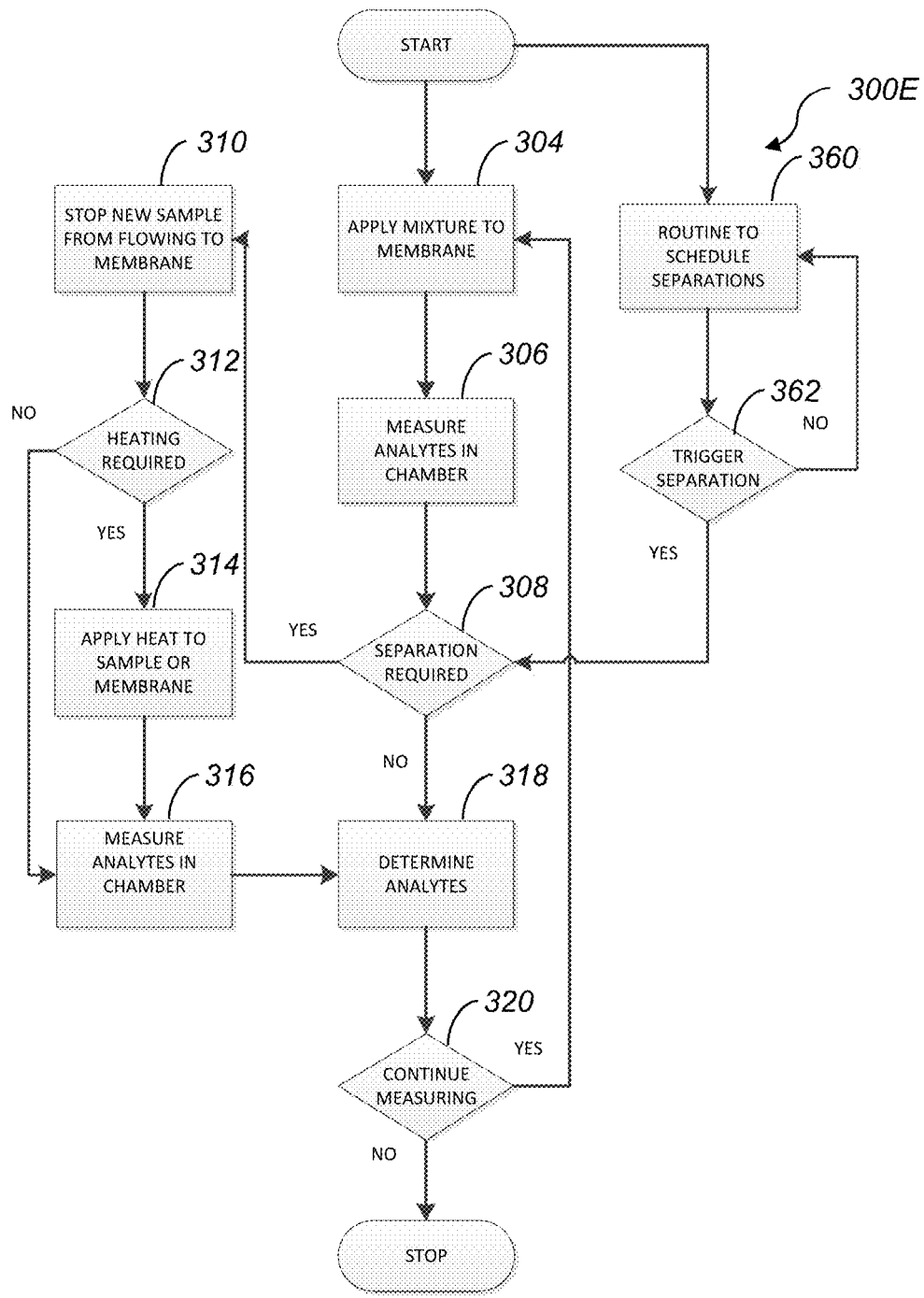

In a different implementation of automated chemical analysis, FIG. 3E depicts a method 300E that schedules routine separations at block 360. For instance, the method 300E may periodically sample the atmosphere or a testing environment, with the test being triggered every few seconds, minutes or hours at block 362. Thereafter, the method 300E proceeds through steps 304-320 as described with respect to any of methods 300A (FIG. 3A), method 300B (FIG. 3B), method 300C (FIG. 3C), or method 300D (FIG. 3D).

Figure 4:
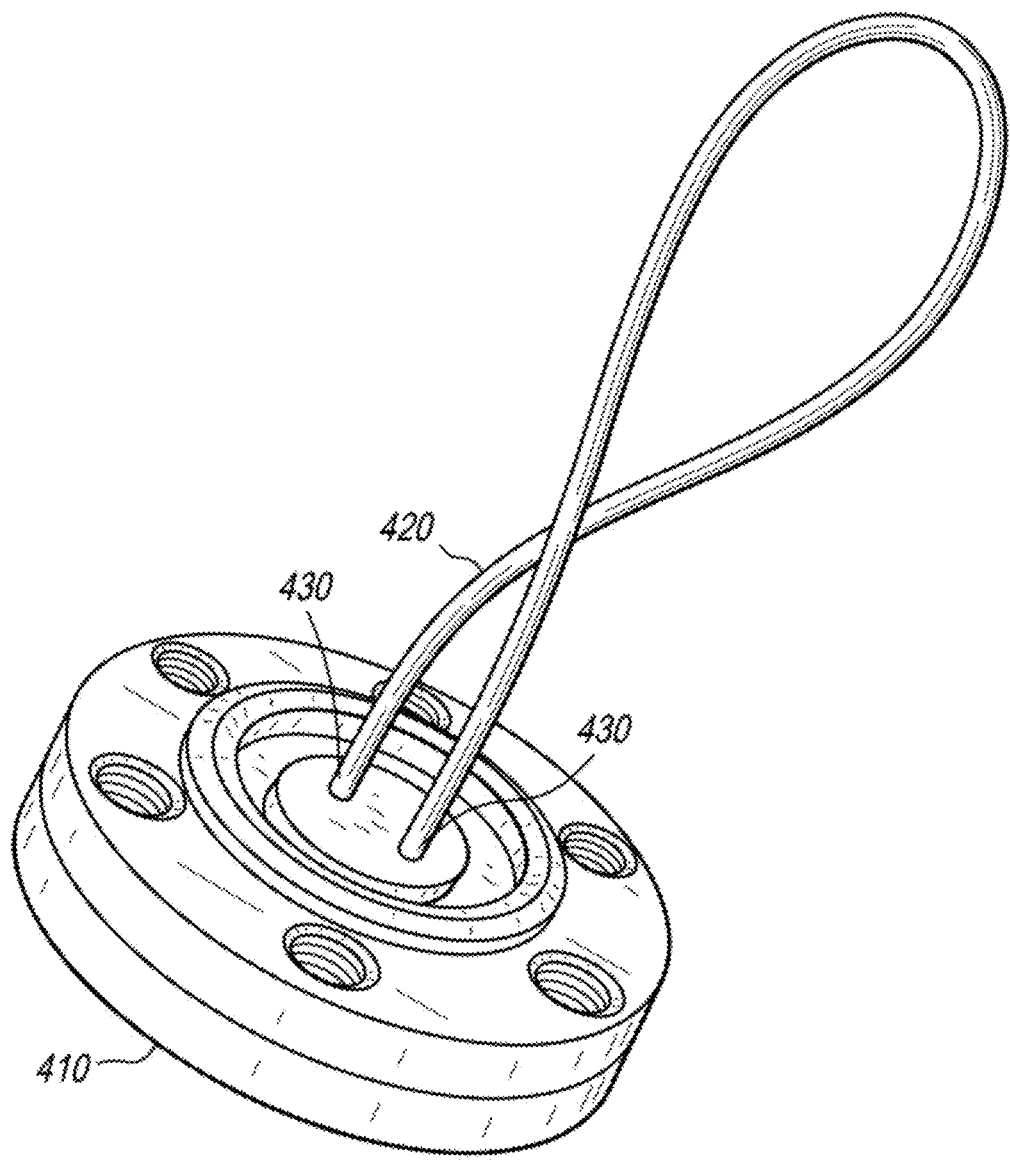
FIG. 4 is a graphical representation of an image of a membrane assembly, in accordance with aspects set forth herein.

FIG. 4 is a graphical representation of an image of a membrane assembly including flange 410 and membrane 420 in the form of a tube. Membrane 420 passes through flange 410 at inlets 430. The use of the term "inlet" throughout this disclosure does not restrict the direction of flow through inlet 430; inlets 430 can receive fluid into membrane 420 or pass fluid out of membrane 420. Membrane 420 can be arranged in a loop, as shown, or straight, or in another configuration.

Figure 5:
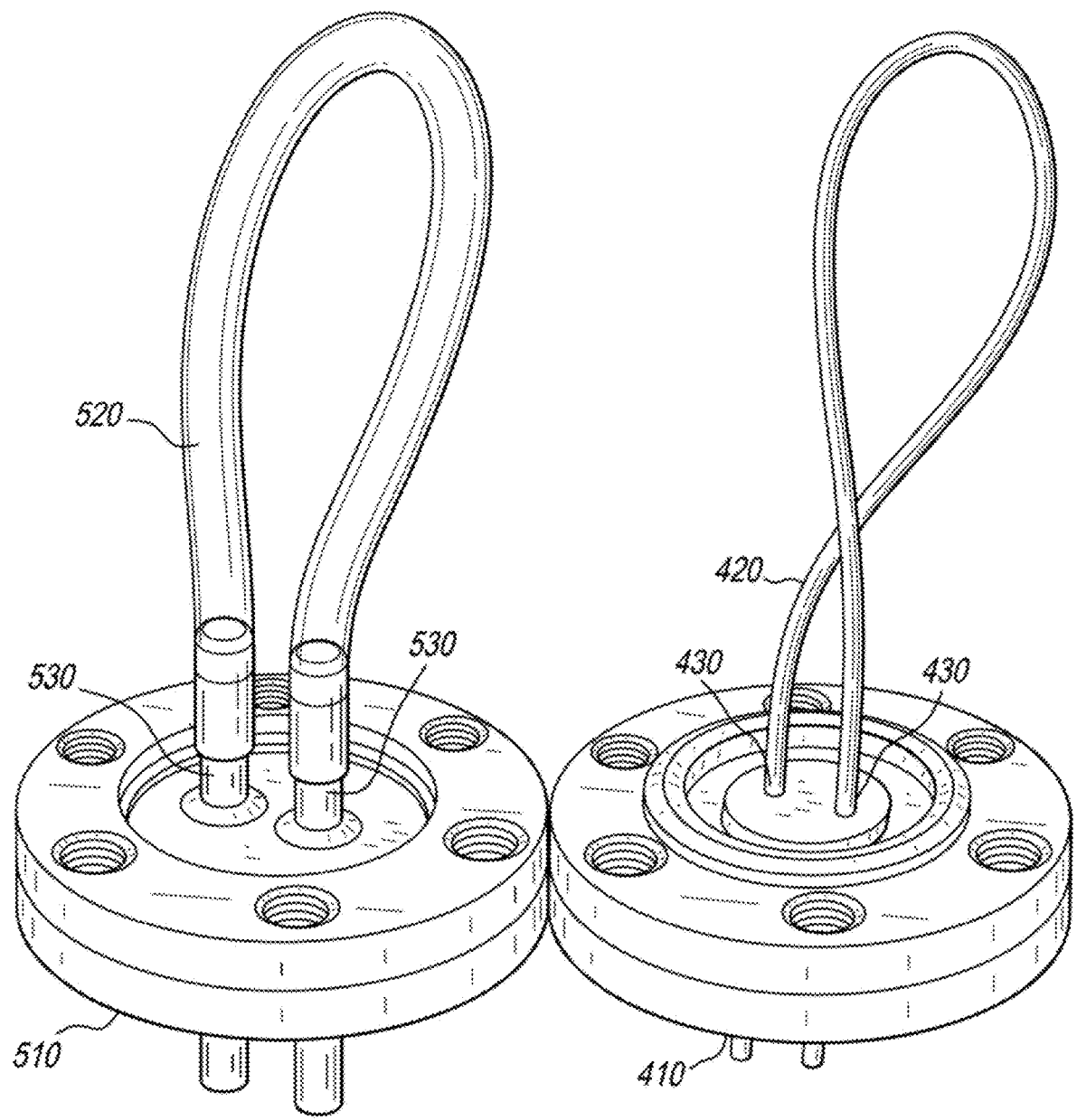
FIG. 5 is a graphical representation of an image of two membrane assemblies, in accordance with aspects set forth herein.

FIG. 5 is a graphical representation of an image of two membrane assemblies using different membranes 420, 520. Each has a flange 410, 510 and inlets 430, 530.

Figure 6:
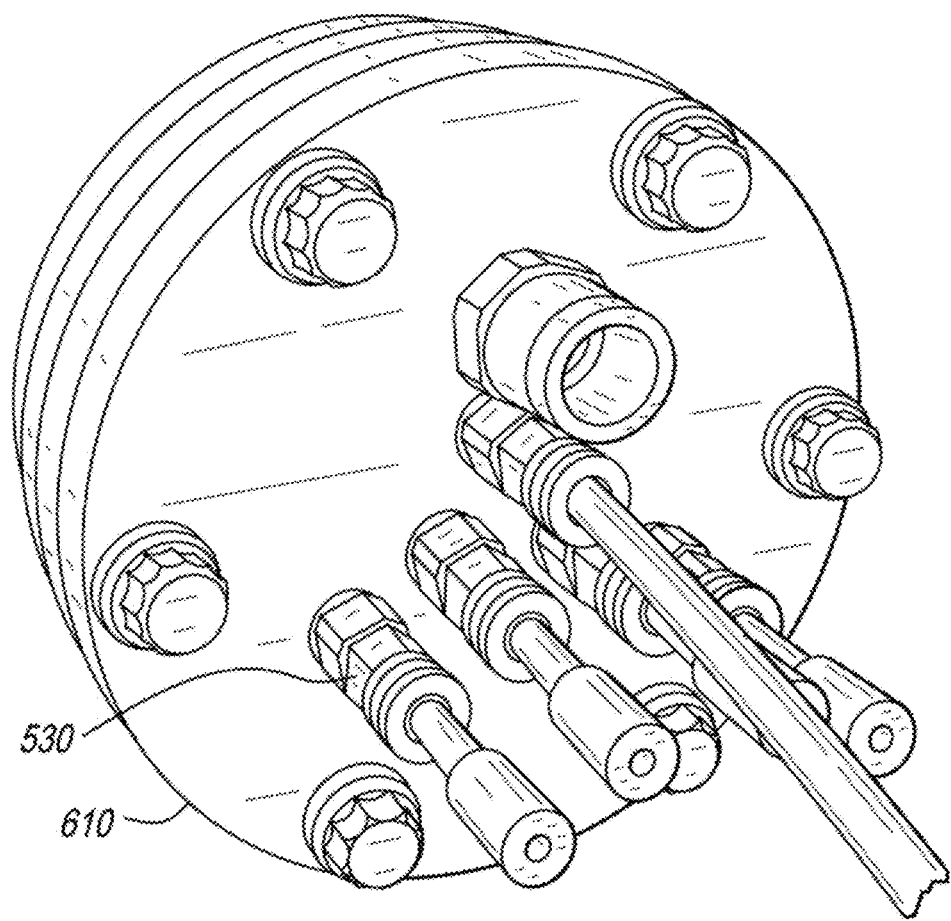
FIG. 6 is a graphical representation of an image of a membrane assembly, in accordance with aspects set forth herein.

FIG. 6 is a graphical representation of an image of a membrane assembly including a flange 610. Through the flange are arranged six inlets 530, one of which is connected to a tube and four of which are capped. As shown, inlets 530 can be different sizes. The six inlets 530 can support, for example, three different membrane tubes (e.g., tubes 420, 520, FIG. 5). The diameter of inlet 530 and the diameter of membrane 520 do not have to be the same. In various aspects, the flange, the membranes, or an assembly of the flange and one or more membrane(s) are line-replaceable units (LRUs), i.e., they can be replaced without sending the system back to the factory for repair.

Figure 7:
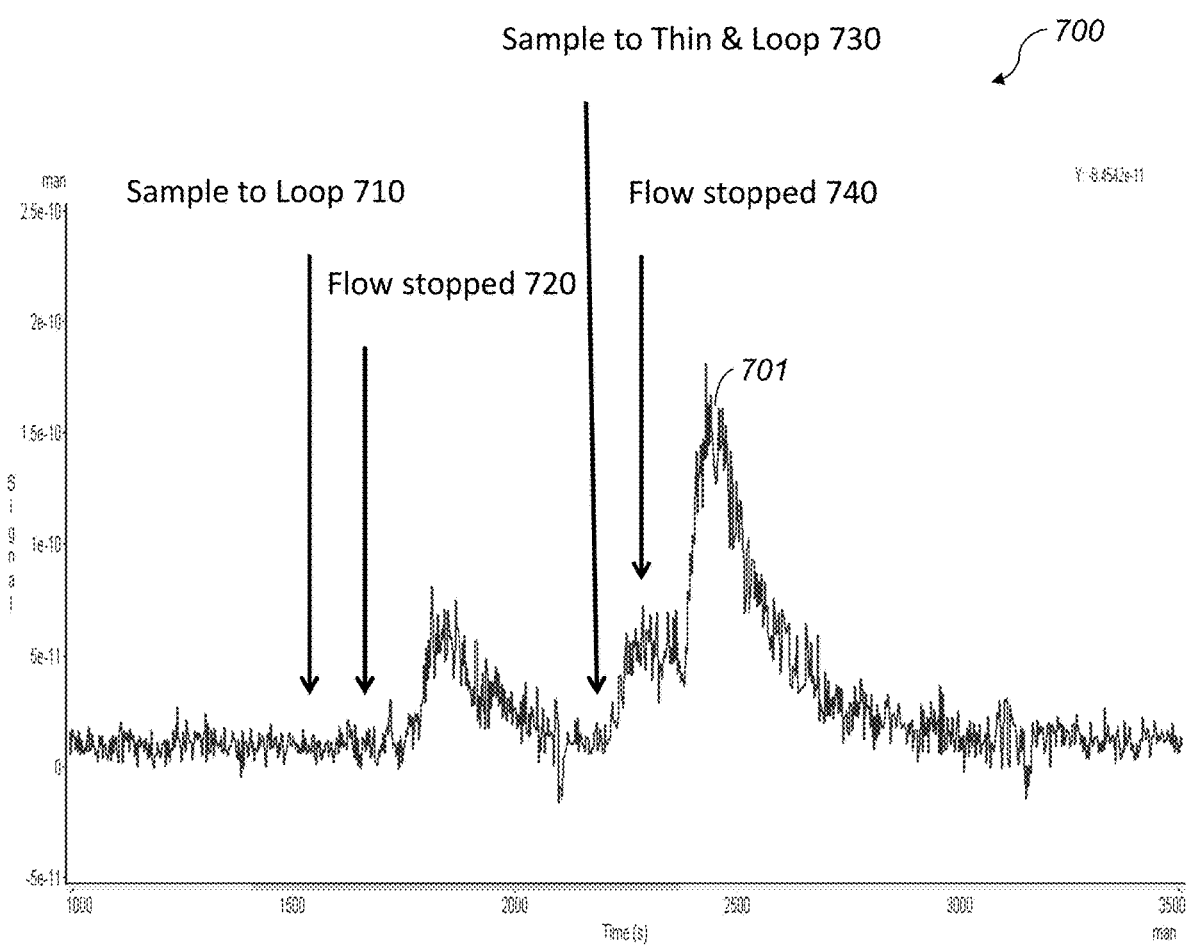
FIG. 7 is a graph of the output of a chemical analyzer, in accordance with aspects set forth herein.

FIG. 7 is a graph 700 of the output of a chemical analyzer (e.g., system 200 of FIG. 2) over time, demonstrating experimental results using the system 200 of FIG. 2 with a single analyte to explain the behavior in general terms. In the example of FIG. 7, at block 710 a sample is applied, e.g., to a loop shaped membrane. Next, at block 720, the flow of the sample is stopped. As may be seen, after the flow is stopped at block 720, the sample signal begins to rise as the sample emerges from the membrane, reaches a peak and declines again. Next, at block 730 the sample is applied to both the thin membrane 261 (FIG. 2) and the loop shaped membrane 260 (FIG. 2). Immediately, the signal rises. Subsequently, the flow is stopped at block 740, and there is a delayed reaction as the signal rises to peak 701, as the analyte elutes from the membrane, and then the signal decays.

Figure 8:
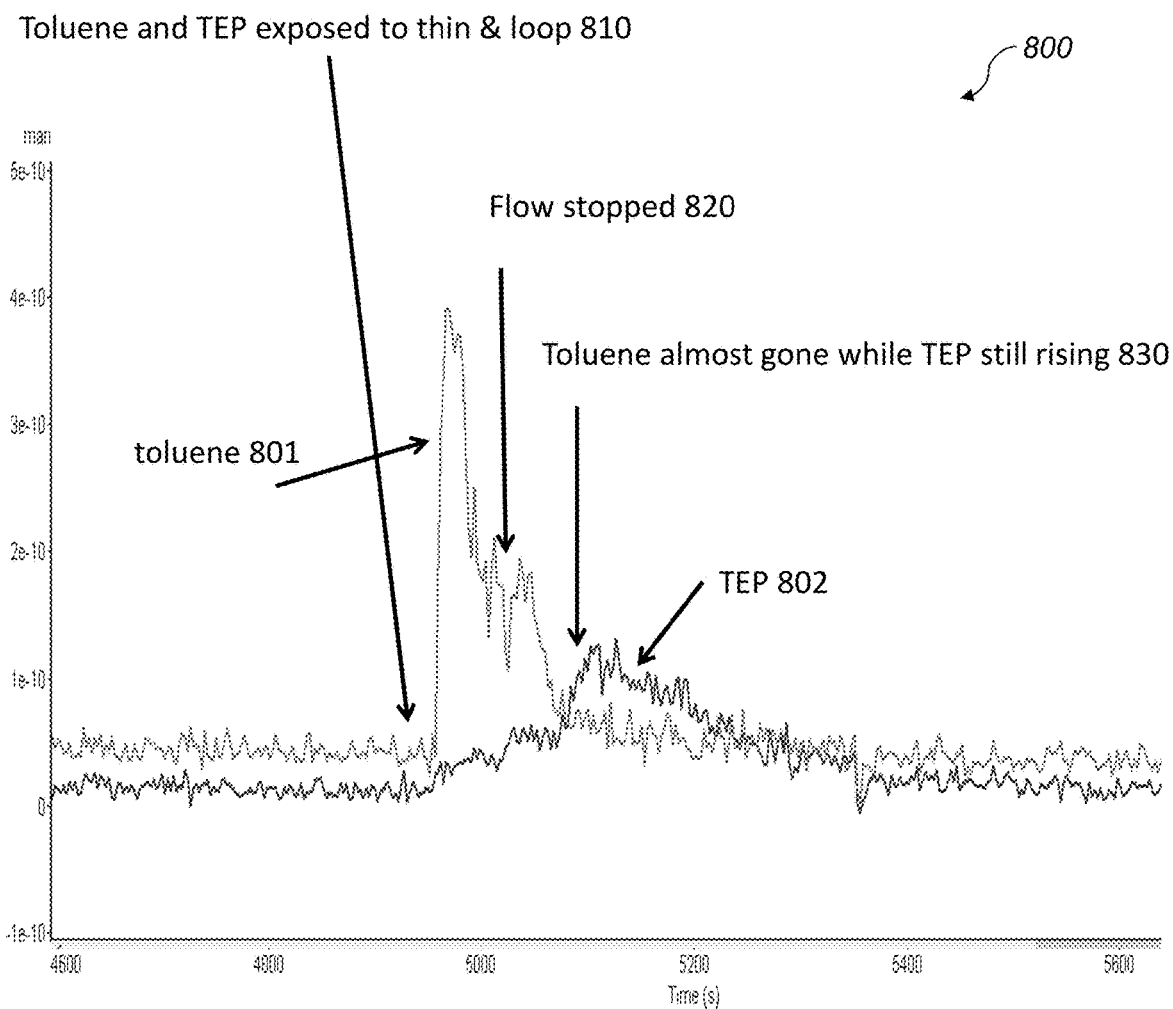
FIG. 8 is a graph of the output of a chemical analyzer, in accordance with aspects set forth herein.

FIG. 8 is a graph 800 of the output of a chemical analyzer (e.g., system 200 of FIG. 2) over time, in which two chemical compounds are applied. Toluene is depicted with curve 801 and triethyl phosphate (TEP) is depicted with curve 802. At block 810, both continue to be applied to the system 200. Because the toluene passes through the membrane faster, a spike is seen. Next, at block 820, the flow is stopped. Now, at block 830, the TEP signal rises as it emerges from the membrane, which the toluene signal declines.

Figure 9:
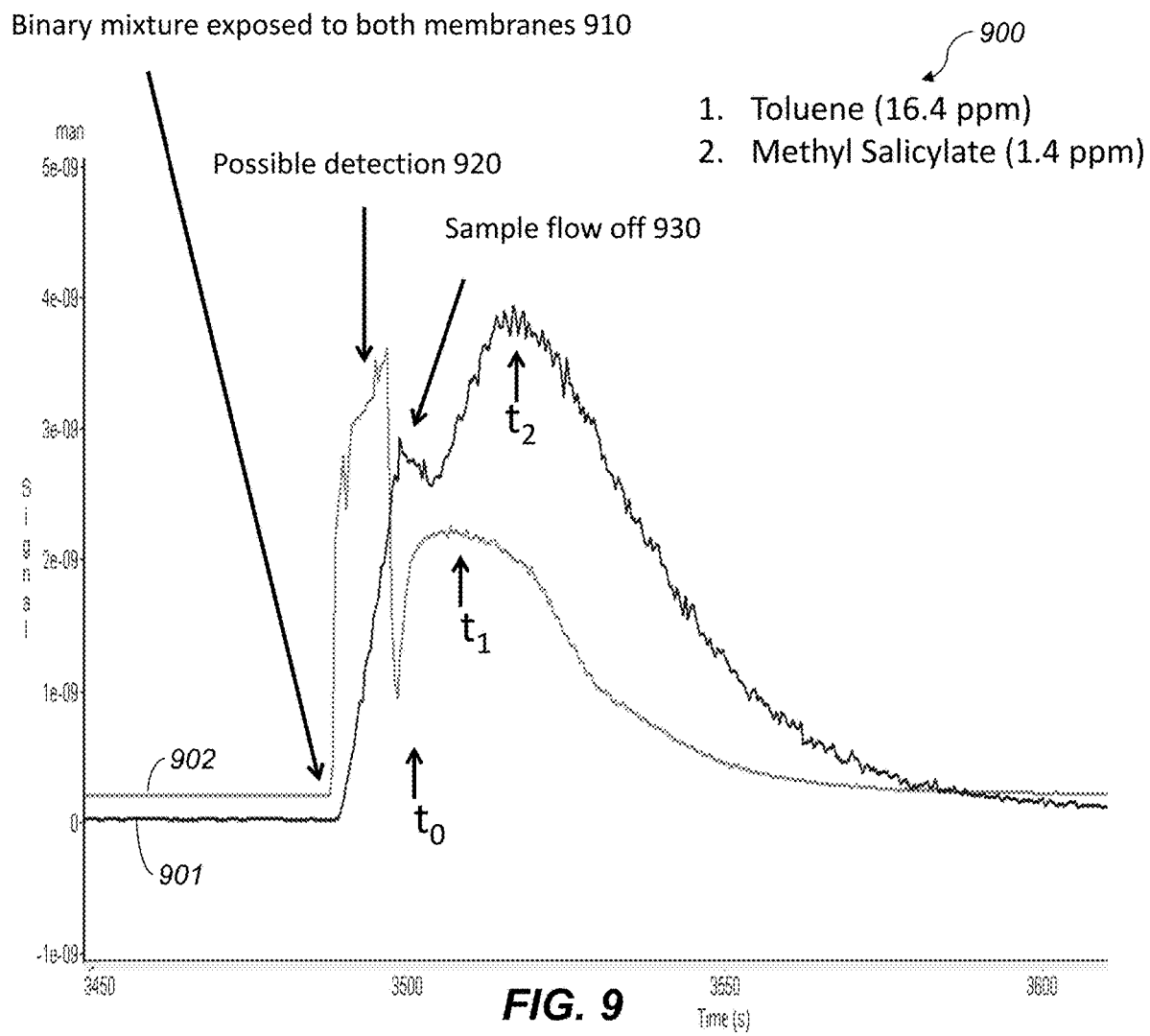
FIG. 9 is a graph of the output of a chemical analyzer, in accordance with aspects set forth herein.

FIG. 9 is a graph of the output of a chemical analyzer (e.g., system 200 of FIG. 2) over time, in which two chemical compounds are applied. At block 910, the binary mixture of toluene (16.4 parts per million) and methyl salicylate (1.4 parts per million) flow into the system 200.

Curve 901 depicts the toluene signal and curve 902 depicts the methyl salicylate signal. As may be seen, the toluene signal rises rapidly and may be possibly detected at block 920. By time t0, the toluene signal declines. At block 930 the sample flow is stopped. By time t1 the toluene signal declines and at time t2 the methyl salicylate signal peaks.

Next FIGS. 10A-11B are used to show that time separation can be combined with analytical approaches (e.g., algorithms) to achieve more accurate identification of the chemicals present in a mixture gas.

Figure 10A:
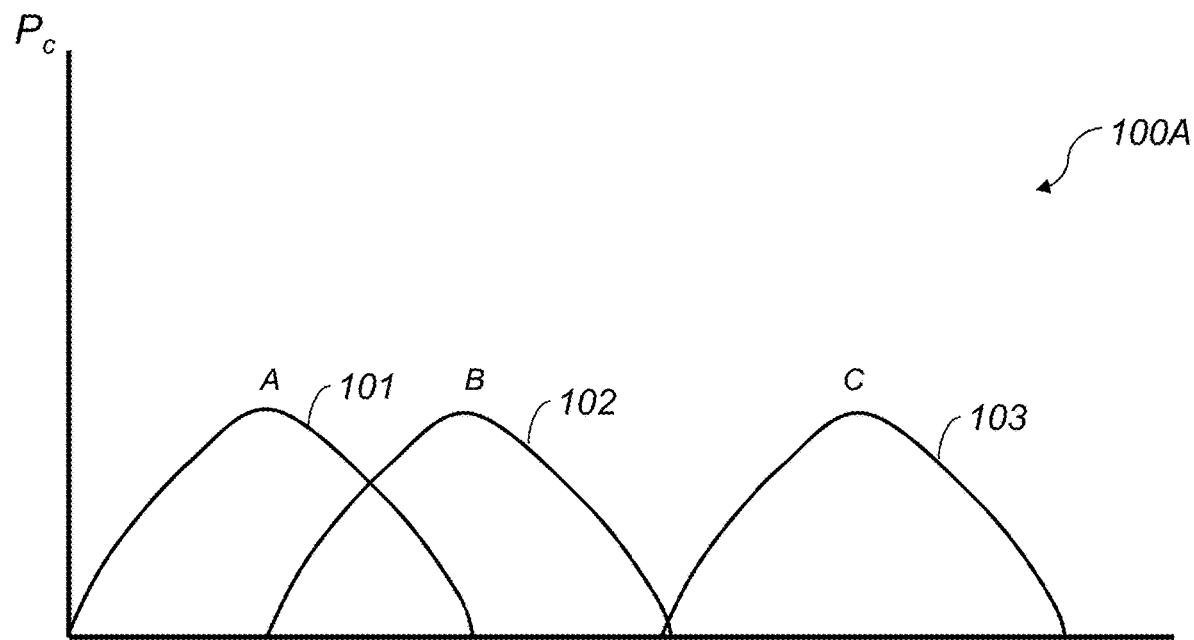
FIGS. 10A-10B are graphs of the output of a chemical analyzer, in accordance with aspects set forth herein.
Figure 10B:
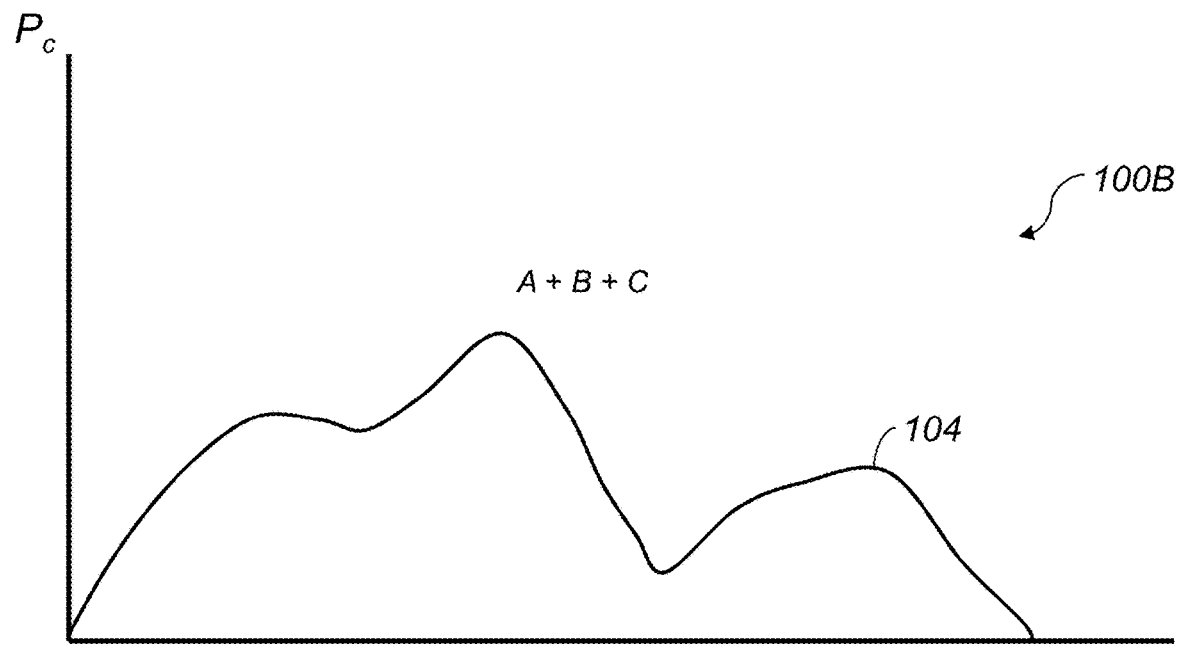

To demonstrate another problem solved by the techniques set forth herein, FIG. 10A is an idealized, conceptual graph 100A of the output of a chemical analyzer (e.g., system 200 of FIG. 2) over time, in which three chemical compounds are applied. In this conceptual graph 100A, an idealized detection reveals that compounds A, B and C are characterized with signals 101, 102 and 103, respectively. Of course, if a single signal (e.g., pressure) is being measured, then these three separate signals 101-103 will not be distinct, but will instead merge into one signal. FIG. 10B depicts the example of FIG. 10A in which the signals have all merged together. In the graph 100B, compounds A, B and C combine to yield a single signal 104. The techniques set forth herein solve this problem, allowing the combined signal 104 of FIG. 10B to be de-convoluted to reveal the individual signals 101-103 of FIG. 10A.

Figure 11A:
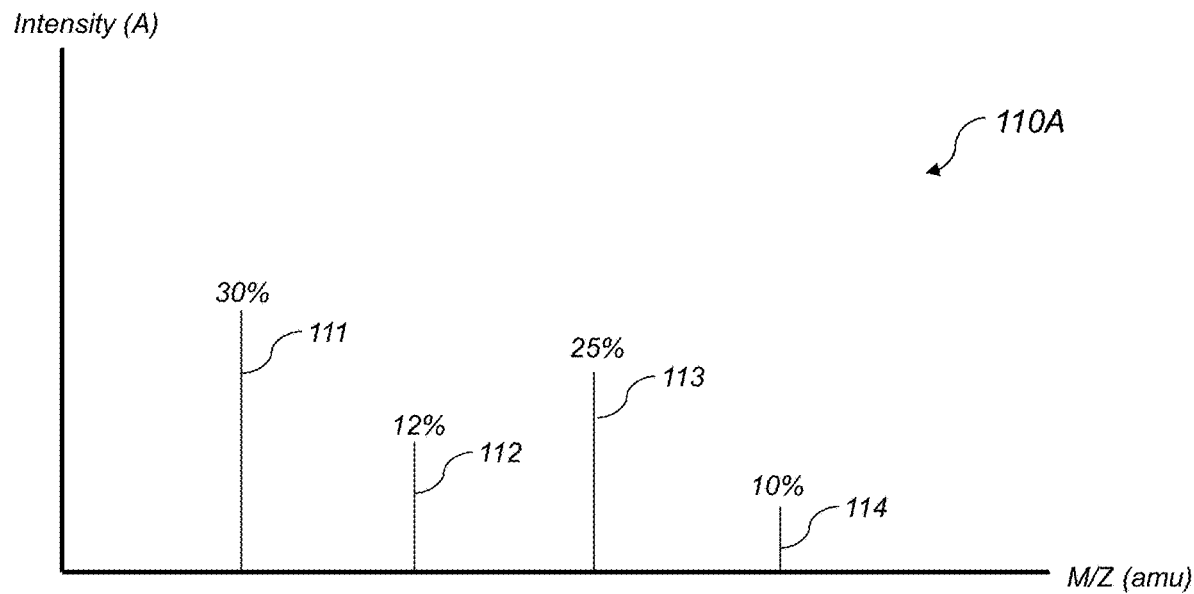
FIGS. 11A-11B are graphs of the output of a chemical analyzer, in accordance with aspects set forth herein.

Continuing along the vein of FIGS. 10A-10B, FIGS. 11A-11B are graphs of the output of a mass spectrometer, showing the signal intensity on the Y-axis and the mass per unit charge in atomic mass units (m/z in amu) on the X-axis. FIG. 11A shows the profile 110A of an example chemical A of interest. In this example, chemical A is characterized by a reading that comprises 30% of line 111, 12% of line 112, 25% of line 113, and 10% of line 114.

Figure 11B:
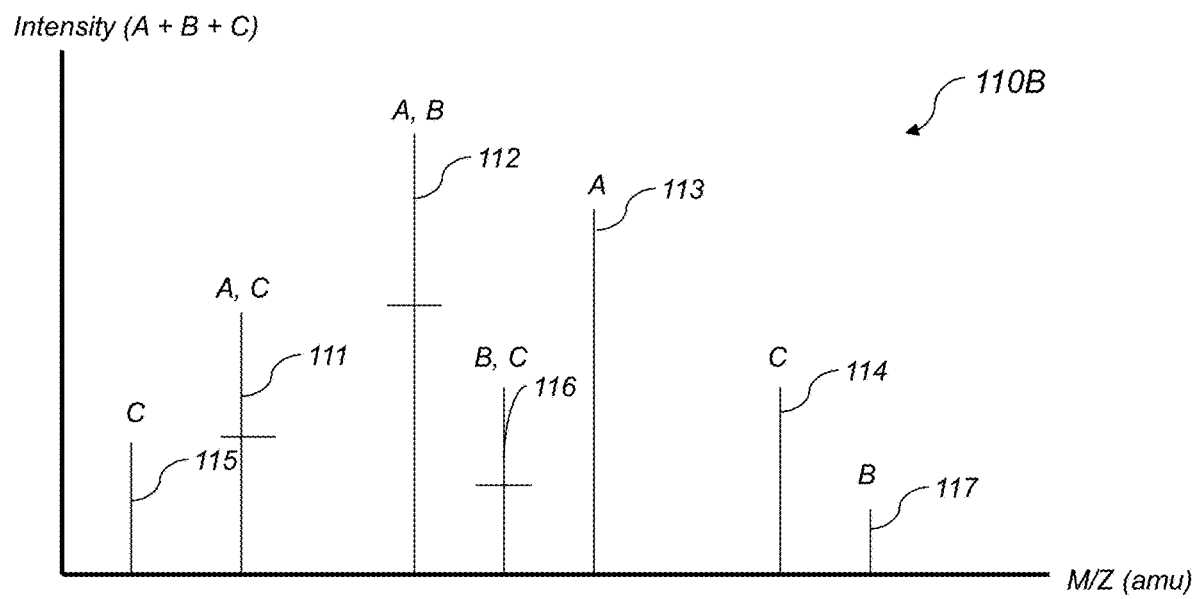

However, if chemical A is present in a mixture of chemicals A, B and C, the output of a mass spectrometer may show profile 110B as depicted in FIG. 11B, after being sent through the system 200 of FIG. 2 and separated using the membrane(s) thereof as described above. In such a case, further analytical or algorithmic separation may be deployed as follows. In profile 110B, in addition to lines 111-114 noted in profile 110A for chemical A, line 115 and line 116 are present as well. Further, the relative signal strength of the different lines 111-116 may be due to the different compounds. For example, in FIG. 11B, line 115 is indicative of only chemical C, line 111 is indicative of a combination of chemicals A and C, line 112 is indicative of a combination of chemicals A and B, line 116 is indicative of a combination of chemicals B and C, line 113 is indicative of only chemical A, line 114 is indicative of only chemical C, and line 117 is indicative of only chemical B.

The algorithmic approach to separation is as follows. Data collected from mass spectrometers typically consists of repeated scans over time, where each scan is an array of mass-to-charge m/z intensities. As the spectrometer is exposed to continuously changing concentrations of molecule fragments, it generates a two-dimensional matrix of m/z intensity values (e.g., as described in FIGS. 11A-11B). Compound identification algorithms examine this matrix to determine the presence or absence of specific target chemicals. The task is typically broken down into two separate subtasks: extraction and search.

In the first subtask, relatively pure spectra are extracted from the data stream. Extraction (also known as deconvolution) is necessary when several different molecules may be simultaneously present in the spectrometer. Some may be increasing in concentration at different rates, while some are decreasing, and others may be part of a relatively stable background. Each molecule in the mix may have unique components in its m/z signature, but they may also have overlapping m/z components. Extraction attempts to correctly identify groups of related m/z intensities that correspond to separate molecules. For details on how AMDIS implements extraction see [Stein 1999]. Examples of other approaches are described in [Liang 1992], [Hanato 1992].

In the second subtask, relatively pure spectra have been extracted from the raw data matrix and each unknown extracted spectrum is compared to a set of known reference spectra (the library). Extracted spectra normally have no exact match in the reference library, so a similarity metric is calculated between the unknown spectrum and each candidate in the library, allowing reference spectra to be ranked in order of closest match. For details on how NIST implements library search see [Stein 1994].

In this application we describe a potentially novel approach to extraction (or deconvolution). Existing approaches, such as those used by AMDIS take advantage of consistencies in how compounds elute from a gas chromatograph column to enter the mass spectrometer. In a GC-MS, ion intensities vary over time according to peak shapes with measurable properties such as height, width, area, tailing etc. Compounds entering the spectrometer through a MIMS system in the presence of complex backgrounds do not follow these predictable peak patterns, however. Our approach (tentatively called mzcc for mass/charge correlation clustering) does not depend on changes of intensity to follow any particular pattern.

Input to the algorithm "mzcc" is a sequence of 3 or more scans, where each scan lists the intensities of a series of m/z ratios. More than 3 scans usually produces better results. Each of the scans must measure the same masses so that their relative values over time can be compared. The algorithm has, for instance, three steps.

Step 1: "boundary selection" selects a time interval to analyze. In real-time detection applications this is typically the most recent scans available, so the algorithm must simply decide how many scans back in time to consider in its analysis.

Step 2: "correlation measurement: calculates e.g. the Pearson product-moment correlation coefficients between each mass and every other mass over the selected time interval. The result of this calculation reveals how strongly the change of intensity over time for each ion correlates with every other ion.

Step 3: "clustering: uses an unsupervised machine learning clustering algorithm to group ions into those that are most closely related. A number of different clustering algorithms exist that can be used for this purpose, e.g. hierarchical clustering.

Each of the three steps can be tuned in a number of different ways to optimize results.

In step 1 the algorithm must consider how quickly the presence of target compounds are expected to change, relative to background compounds. Techniques such as evolving factor analysis may be used to identify relatively noisy or more stable regions to select an analysis boundary. Deskewing of data collected over time is important because subsequent steps rely on an estimate of simultaneous measurements of m/z intensities.

In step 2 a threshold may be applied to the results to reduce the number of masses under consideration. It may also be helpful to weigh the relative importance of higher masses, requiring tighter correlations between lower masses than higher masses. Conversion of correlation measures to a distance metric used in step 3 may affect results. Options include using (1−C) or sqrt(1−C) or −log(C) or (1/C)−1

In step 3, the choice of clustering algorithm, as well as parameters to the algorithms such as the minimum cluster sizes, minimum distances between elements, etc. can have significant impact on the results. In some cases a single mass may be present in more than one simultaneously occurring compound. For example mz 127 is present in Sulfur hexafluoride and in Triethyl phosphate, but one compound may be increasing in concentration while the other is decreasing. In this case 127 will not correlate well with the other masses present in either of the other compounds. Techniques such as "soft clustering" (where each element is not necessarily assigned to only a single cluster) may help. It is also possible to influence the clustering algorithm with knowledge of the target compounds.

The following references listed below are hereby incorporated by reference herein in their entirety:

Stein 1999: An Integrated Method for Spectrum Extraction and Compound Identification from GC/MS Data, Stephen E. Stein, Journal of the American Society for Mass Spectrometry 1999.

Liang 1992: Heuristic evolving latent projections: resolving two-way multicomponent data, Olav M. Kvalheim and Yi Zeng. Liang, Analytical Chemistry 1992.

Hanato 1992: Hantao, L. W., Aleme, H. G., Pedroso, M. P., Sabin, G. P., Poppi, R. J., & Augusto, F. (2012). Multivariate curve resolution combined with gas chromatography to enhance analytical separation in complex samples: a review. Analytica chimica acta, 731, 11-23.

To the extent that the claims recite the phrase "at least one of" in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof. "At least one of element A, element B, and element C" is not intended to be limited to at least one of an element A, at least one of an element B, and at least one of an element C.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

What is claimed is:

1. A device for chemical analysis of a sample, the device comprising:
   a housing containing an interior chamber of the device;
   an inlet on the housing for introducing the sample into the interior chamber;
   a pump connected to the housing to form a partial vacuum in the interior chamber;
   multiple membranes having different response times to different constituents of the sample, the multiple membranes comprising a first membrane and a second membrane, wherein at least one of the first membrane and the second membrane comprises a tubular portion; and
   a detector for detecting the different constituents of the sample after interaction with the multiple membranes, wherein the device is configured to
   introduce the sample to the multiple membranes;
   stop the flow of the sample to the multiple membranes after a period of time to facilitate separation of the sample; and
   continuously detect analytes in the interior chamber after the sample interacts with a first of the multiple membranes to determine a preliminary result, and after the sample interacts with a second of the multiple membranes to determine a final result.

2. The device of claim 1, wherein the detector comprises a mass spectrometer and an ion source is disposed within the interior chamber.

3. The device of claim 1, wherein at least another of the multiple membranes comprises a flat portion disposed between the inlet and the interior chamber.

4. The device of claim 1, wherein the multiple membranes comprise a third membrane.

5. The device of claim 1, wherein the multiple membranes are exposed to the sample sequentially.

6. The device of claim 1, wherein the multiple membranes are exposed to the sample in parallel.

7. The device of claim 1, wherein the multiple membranes have different response times to multiple constituents having a specific mass to charge ratio.

8. The device of claim 1, further comprising a heating element to facilitate the different response times of the different constituents.

9. The device of claim 1, wherein the different constituents comprise different molecules.

10. The device of claim 1, wherein the detector is configured to perform a first detection of the sample after interacting with a first of the multiple membranes to determine a preliminary result, and if the preliminary result indicates a likelihood of an outcome, perform a second detection of the sample after interacting with a second of the multiple membranes to determine a final result.

11. The device of claim 1, wherein the multiple membranes are exposed to the sample sequentially.

12. The device of claim 1, wherein the multiple membranes are exposed to the sample in parallel.

13. The device of claim 1, wherein the multiple membranes have different response times to multiple constituents having a specific mass to charge ratio.

14. The device of claim 1, wherein the different constituents comprise different molecules.

15. A method for chemical analysis of a sample, the method comprising:
   introducing a sample to multiple membranes having different response times to different constituents of the sample;
   separating the different constituents of the sample due to the different response times of the multiple membranes;
   detecting the different constituents of the gas after separating with the multiple membranes;
   continuously detecting analytes in the interior chamber after the sample interacts with a first of the multiple membranes to determine a preliminary result, and after the sample interacts with a second of the multiple membranes to determine a final result.

16. The method of claim 15, further wherein the separating the different constituents of the sample includes starting and stopping a flow of the sample.

17. The method of claim 15, wherein the introducing comprises introducing the sample to a first of the multiple membranes at a first time and a second of the multiple membranes at a second time after the first time.

18. The method of claim 17, further comprising detecting a preliminary result after introducing the sample to the first of the multiple membranes at the first time, and if the preliminary result indicates a likelihood of an outcome, detecting a final result after introducing the sample to the second of the multiple membranes at the second time.

19. The method of claim 15, wherein the introducing comprises introducing the sample to the multiple membranes at a same time.

20. A device for chemical analysis of a sample, the device comprising:
   a housing containing an interior chamber of the device;
   an inlet on the housing for introducing the sample into the interior chamber;
   a pump connected to the housing to form a partial vacuum in the interior chamber;
   multiple membranes having different response times to different constituents of the sample, the multiple membranes comprising a first membrane and a second membrane, wherein at least one of the first membrane and the second membrane comprises a tubular portion; and
   a detector for detecting the different constituents of the sample after interaction with the multiple membranes, the detector comprising a mass spectrometer; and
   at least one heating element disposed near at least one of the multiple membranes, wherein the at least one heating element is configured to heat the at least one of the multiple membranes to facilitate different response times of the different constituents,
   wherein the device is configured to
   introduce the sample to the multiple membranes;
   stop the flow of the sample to the multiple membranes after a period of time to facilitate separation of the sample; and
   continuously detect analytes in the interior chamber after the sample interacts with a first of the multiple membranes to determine a preliminary result, and after the sample interacts with a second of the multiple membranes to determine a final result.

* * * * *